US007767468B2

(12) United States Patent
Shuber et al.

(10) Patent No.: US 7,767,468 B2
(45) Date of Patent: Aug. 3, 2010

(54) REPETITIVE AFFINITY SEPARATION AND USES THEREFOR

(75) Inventors: Anthony P. Shuber, Mendon, MA (US); Duncan Whitney, Sudbury, MA (US)

(73) Assignee: EXACT Sciences Corporation, Madison, WI (US)

( * ) Notice: Subject to any disclaimer, the term of this patent is extended or adjusted under 35 U.S.C. 154(b) by 653 days.

(21) Appl. No.: 10/982,733

(22) Filed: Nov. 5, 2004

(65) Prior Publication Data

US 2005/0247563 A1 Nov. 10, 2005

Related U.S. Application Data

(60) Provisional application No. 60/517,623, filed on Nov. 5, 2003, provisional application No. 60/530,461, filed on Dec. 16, 2003.

(51) Int. Cl.
*G01N 33/544* (2006.01)
(52) U.S. Cl. ............... 436/535; 435/7.1; 435/283.1; 435/287.1; 435/287.2; 435/288.3; 435/288.7; 204/450; 356/344
(58) Field of Classification Search ............ 435/7.1, 435/283.1, 287.1, 287.2, 288.3–5, 288.7; 422/50, 55–59, 68.1; 436/518, 524, 529, 436/531, 535; 356/344; 204/450
See application file for complete search history.

(56) References Cited

U.S. PATENT DOCUMENTS

| 4,154,669 | A | * | 5/1979 | Goetz ........................ 204/645 |
| 5,143,854 | A | | 9/1992 | Pirrung et al. |
| 5,286,434 | A | * | 2/1994 | Slater et al. ................. 204/457 |
| 5,330,892 | A | | 7/1994 | Vogelstein et al. |
| 5,352,775 | A | | 10/1994 | Albertsen et al. |
| 5,405,519 | A | * | 4/1995 | Schwartz .................... 204/609 |
| 5,427,729 | A | * | 6/1995 | Dubrow ...................... 264/232 |
| 5,478,893 | A | | 12/1995 | Ghosh et al. |
| 5,482,863 | A | | 1/1996 | Knobel et al. |
| 5,527,676 | A | | 6/1996 | Vogelstein et al. |
| 5,532,108 | A | | 7/1996 | Vogelstein |
| 5,549,796 | A | | 8/1996 | Chu et al. |
| 5,741,650 | A | | 4/1998 | Lapidus et al. |
| 5,922,591 | A | * | 7/1999 | Anderson et al. ........ 435/287.2 |
| 5,932,711 | A | | 8/1999 | Boles et al. |
| 6,007,690 | A | * | 12/1999 | Nelson et al. ............... 204/601 |
| 6,214,187 | B1 | | 4/2001 | Hammond et al. |
| 6,238,927 | B1 | | 5/2001 | Abrams et al. |
| 6,251,660 | B1 | | 6/2001 | Muir et al. |
| 6,287,850 | B1 | | 9/2001 | Besemer et al. |
| 6,399,365 | B2 | | 6/2002 | Besemer et al. |
| 6,503,718 | B2 | | 1/2003 | Shuber et al. |
| 6,551,817 | B2 | | 4/2003 | Besemer et al. |
| 6,653,121 | B2 | | 11/2003 | May |
| 6,664,104 | B2 | | 12/2003 | Pourahmadi et al. |
| 6,875,619 | B2 | * | 4/2005 | Blackburn .................... 506/9 |
| 7,217,542 | B2 | * | 5/2007 | Tyvoll et al. ............... 435/91.1 |
| 2002/0119480 | A1 | | 8/2002 | Weir et al. |
| 2002/0172955 | A1 | | 11/2002 | Adams et al. |
| 2002/0197614 | A1 | | 12/2002 | Weir et al. |
| 2003/0138774 | A1 | | 7/2003 | Jones et al. |
| 2003/0170635 | A1 | | 9/2003 | Hammond et al. |
| 2004/0152208 | A1 | * | 8/2004 | Hutchinson ................. 436/518 |
| 2005/0079519 | A1 | | 4/2005 | Boles et al. |
| 2006/0057566 | A1 | * | 3/2006 | Van Ness et al. ................ 435/6 |
| 2006/0088867 | A1 | | 4/2006 | Weir et al. |

FOREIGN PATENT DOCUMENTS

| WO | WO-92/10092 | 6/1992 |
| WO | WO-98/51823 | 11/1998 |
| WO | WO-99/45374 | 9/1999 |
| WO | WO-00/50644 | 8/2000 |
| WO | WO-00/60120 | 10/2000 |
| WO | WO-2004/065543 | 8/2004 |

OTHER PUBLICATIONS

Carle et al., Electrophoretic Separations of Large DNA Molecules by Periodic Inversion of the Electric Field, 1986, Science, vol. 232., No. 4746, pp. 65-68.*
Baba et al. "Specific Base Recognition of Oligodeoxynucleotides by Capillary Affinity Gel Electrophoresis Using Polyacrylamide-Poly(9-vinyladenine) Conjugated Gel" (1992), Analyt. Chem. 64:1920-1924.
Bille et al. "Effect of the microenvironment of the kinetic properties of immobilized enzymes" (1989), Eur. J. Biochem. 180:41-47.
Chu et al. "Separation of Large DNA Molecules by Contour-Clamped Homogeneous Electric Fields" (1986), Science 234:1582-1585.
Chu et al. "Use of Affinity Capillary Electrophoresis to Measure Binding Constants of Ligands to Proteins" (1992), J. Med. Chem. 35:2915-2917.
Gardiner et al. "Fractionation of Large Mammalian DNA Restriction Fragments Using Vertical Pulsed-Field Gel Electrophoresis" (1986), Somatic Cell Molec. Genet. 12:185-195.

(Continued)

*Primary Examiner*—Melanie J Yu
(74) *Attorney, Agent, or Firm*—Casimir Jones, S.C.

(57) ABSTRACT

Improved methods for the separation, isolation, enrichment, or detection of target molecules, such as nucleic acids and proteins, within dilute or heterogeneous samples, such as bodily fluids, excreta or tissue samples, are disclosed. The methods include repetitively and rapidly passing a sample across at least one region of a conduit in which at least one region includes a binding partner specific for the target molecule. In certain methods, at least one other region includes binding partners specific for non-target molecules. The sample may be passed over the binding partner in the same direction if the conduit is a loop or in an antiparallel direction (i.e., back and forth over the binding partner). In an embodiment, the sample is electrophoresed through or over an electrophoretic medium, in which at least one region includes a binding partner for the target molecule. The invention also provides apparatus and sample preparation systems adapted for use in the methods.

13 Claims, 7 Drawing Sheets

OTHER PUBLICATIONS

Holtz et al. "Polymerized colloidal crystal hydrogel films as intelligent chemical sensing materials" (1997), Nature 389:829-832.

Horejsi et al. "Studies on Phytohemagglutinins" (1974), Biochim. Biophys. Ada 336:338-343.

Li et al. "Detection of MET oncogene amplification in hepatocellular carcinomas by comparative genomic hybridization on microarrays" (2003), Gene Ther. Mol. Biol., 7:99-102.

Rehman et al. "Immobilization of acrylamide-modified oligonucleotides by co-polymerization" Nucleic Acids Research, 1999, vol. 27, No. 2.

Schwartz et al. "Separation of Yeast Chromosome-Sized DNAs by Pulsed Field Gradient Gel Electrophoresis" (1984), Cell 37:67-75.

Surolia et al. "Protein A: nature's universal anti-antibody" (1981), Trends Biochem. Sci. 7:74-76.

Wang et al. "Biocatalytic plastics as active and stable materials for biotransformations" (1997), Nature Biotechnology 15:789-793.

Carle et al. "Electrophoretic Separations of Large DNA Molecules by Periodic Inversion of the Electric Field" 1986, 232:65-69.

Timofeev et al., "Regioselective immobilization of short oligonucleotides to acrylic copolymer gels," Nucleic Acids Research, 1996, vol. 24, No. 16.

Giddings, "Unified Separation Sciences," University of Utah, Chapter 8, pp. 155-170.

* cited by examiner

REPETITIVE AFFINITY SEPARATION AND USES THEREFOR

RELATED APPLICATIONS

This application claims priority to U.S. Ser. No. 60/517,623, filed Nov. 5, 2003, and U.S. Ser. No. 60/530,461, filed Dec. 16, 2003, each of which is incorporated herein by reference in its entirety.

FIELD OF THE INVENTION

The invention relates to the methods for separating, isolating, enriching or detecting target molecules from a sample, for example rare or dilute target molecules.

BACKGROUND OF THE INVENTION

A variety of techniques have been developed for separating, isolating, enriching, and detecting target molecules in a sample. These techniques include chromatography, (e.g., paper, liquid, such as high performance liquid phase (HPLC)); electrophoresis (e.g., capillary and slab electrophoresis, such as agarose or polyacrylamide gel electrophoresis (PAGE), affinity electrophoresis); affinity purification (e.g., immunoaffinity column); nucleic acid hybridization (e.g., Southern and Northern hybridizations, nucleic acid arrays); and antibody based methods (e.g., Western hybridization, antibody arrays).

Gel electrophoresis is one of the best known methods for separating, purifying and characterizing charged molecules, particularly macromolecules such as proteins or nucleic acids (Freifelder, ed., *Physical Biochemistry,* 2nd Ed., W.H. Freeman and Company, San Francisco (1982), pp. 276-310), In electrophoretic separations, charged molecules migrate through a supporting medium under the influence of an electric field. The supporting medium acts to suppress convection and diffusion and, in some circumstances, can act as a sieve. Electrophoresis can be used to separate molecules based on size, charge, conformation or combinations of these properties.

Most frequently, electrophoresis is carried out using a constant voltage applied across two fixed electrodes located at opposite ends of a gel medium, which results in a linear constant voltage gradient of fixed orientation. However, for very large DNA molecules (i.e., 30-2000 kb), the polymeric chain orients with the field and snakes through the gel, rendering the sieving action of the electrophoretic medium ineffective. In order to separate large DNA molecules, "field inversion" electrophoresis, in which the field orientation is reversed cyclically (see, e.g., Cane et al. (1986), *Science* 232:65-68), and 'pulsed field" electrophoresis (see, e.g., Schwartz et al. (1984), *Cell* 37:67), in which the field is reoriented at oblique angles cyclically, have been developed. Other approaches that included alternating or varied electric field include transverse alternating field electrophoresis (TAFE) and contour-clamped homogeneous electric field (CHEF) electrophoresis (see, e.g., Gardiner et al. (1986), *Somatic Cell Molec. Genet.* 12:185-195; Chu et al. (1986), *Science* 234:1582-1585; U.S. Pat. No. 5,549,796).

In affinity electrophoresis, the support medium (e.g., gel) contains a binding partner that interacts specifically or non-specifically with one or more desired target molecules and aids in the separation of target molecules from non-target molecules during electrophoretic migration. For example, affinity electrophoresis has been used to measure the binding affinity of proteins (Horcjsi et al. (1974), Biochim. Biophys. Ada 3 36:338-343; Chu et al. (1992), J~Med. Chem. 35:2915-2917). In addition, vinyl-adenine-modified polyacrylamide electrophoretic media have been used to enhance the resolution of nucleic acids in capillary electrophoresis (Baba et al. (1992), Analyt. Chem. 64:1920-1924).

PCT Intl. Pub. No. WO 98/51823 describes methods of detecting target molecules using electrophoresis media containing immobilized polynucleotides as the binding for the target molecule. The target molecules are typically nucleic acids, but also can include other molecules that bind to nucleic acids, such as DNA-binding proteins and aptamer binding partners.

PCT Intl. Pub. No. WO 99/45374 describes an affinity electrophoresis process in which the direction of electrophoresis is varied in a cyclical manner, while synchronously changing one or more properties of the electrophoretic medium between two states, which alternatively favor and disfavor specific reversible binding of target molecules to the binding partners that are immobilized within the medium.

PCT Intl. Pub. No. WO 00/50644 describes methods for purifying DNA using binding partners immobilized within an electrophoretic medium. In some embodiments, the electric field is increased in strength to release target molecules that have bound to the binding partners, and in some embodiments, the direction of the electric field is reversed to remove the released target molecules for collection.

Samples that are extremely dilute with respect to the target molecules or in which the target molecule is rare, or samples that are extremely heterogeneous with respect to highly similar non-target molecules, pose particular problems of separation and detection. For example, human stool samples examined for the diagnosis of colon cancer contain large amounts of bacterial DNA and protein relative to human DNA and protein, and large amounts of normal human DNA and protein relative to, for example, a DNA or protein that is indicative of a cancer-associated mutation. Similarly, human blood samples examined for the presence of pathogenic infections contain large amounts of human DNA and proteins relative to any pathogen-derived DNA or proteins.

Similarly, environmental (e.g., watershed) or industrial (e.g., food processing) samples examined for the presence of pathogens are extremely dilute with respect to any pathogen-derived DNA or proteins. Moreover, target and non-target biomolecules that contain only slight structural differences, for example, a point mutation in a protein or nucleic acid, cannot be easily separated from normal molecules by standard electrophoretic techniques.

A need therefore remains for improved methods for the separation, isolation, enrichment and detection of target molecules in dilute or heterogeneous test samples.

SUMMARY OF THE INVENTION

The present invention provides improved methods for separating, isolating, enriching, or detecting target molecules in a sample. A sample containing a target molecule of interest (e.g., a nucleic acid, protein, or cell expressing the target molecule) is repeatedly exposed to a binding partner on a solid support or in a medium, for example, by the rapid flow of the sample past a binding partner for the target molecule. The repetitive and rapid nature of the methods of the invention provides both a enhanced efficiency of recovery of target molecules from a sample while maintaining specificity of binding of the target molecule to its binding partner. Each exposure of the sample to the binding partner provides the target molecule with an opportunity to bind its binding partner, thereby enhancing the total number of target molecules bound to its binding partner with each exposure.

The rate of flow of the sample past its binding partner depends upon the degree of specificity of binding between the target molecule and binding partner that is desired, The faster the rate of flow of a sample past its binding partner, the more specific the binding between the target molecule and the binding partner. The slower the rate of flow of a sample over the binding partner, the more likely a non-target molecule will bind to the binding partner for the target molecule, Thus, rare target molecules are recovered from dilute or heterogeneous samples that are not recovered using standard methods and with a minimum of background due to rapid and repeated passage of the sample over the binding partner.

The binding partner may be attached to a solid support or may be embedded within a medium (e.g., agarose, polyacrylamide medium, beads), through which, or past which, the sample passes.

The movement of the sample is driven by a motive force, for example a mechanical means (e.g., vacuum, positive pressure, or gravity) or electrophoretic means (e.g., electric current), for example.

In an embodiment, the sample is repeatedly exposed to a number of binding partners in separate regions of a medium or solid support, for simultaneous separation or isolation of a number of target molecules from the sample. In some embodiments, at least one binding partner is specific for a non-target molecule or molecules, such that non-target molecules are simultaneously and repeatedly removed from the sample with each passage of the sample through the medium. The repeated movement of the sample may be in the same direction with each repetition (e.g., it is a continuous flow or cycle in the same direction) or may be in a substantially opposite direction (e.g., the sample is moved forward and backward past the binding partner). In a preferred embodiment, the sample is electrophoresed through a medium containing at least one binding partner in one direction, the polarity of the electric current is then reversed, and the sample is electrophoresed back through the medium in the opposite direction, repeating the forward-backward cycle as desired.

In an embodiment of the invention, the target molecule remains bound to its binding partner throughout the repeated exposure or cycling of the sample past the binding partner. For example, the conditions (e.g., temperature or pH) of the medium through which the sample flows are not changed such that the target molecule disassociates from its binding partner.

In another embodiment, the timing of each exposures of the sample with the target molecule binding partner remains substantially constant. For example, if a sample is electrophoresed in a first direction through a medium containing a binding partner for a target molecule for a certain period of time at a certain voltage, the timing and voltage of electrophoresis of the sample in the reverse direction is substantially the same.

In another embodiment, the target molecule is exposed to a binding partner under conditions that minimize the amount of time a non-target molecule is exposed to the binding partner, thereby minimizing background binding of the non-target molecule to the binding partner. By altering the conditions of the medium (e.g., agarose concentration of the gel in electrophoresis) or the motive force (e.g., pump speed or electric current), the target molecule with rapidly traverse the region of the solid support or medium containing the binding molecule such that specificity is optimized.

In an embodiment, the solid support is a cuvette or chip, for example a silicon chip. In an embodiment, the solid support has at least one channel through which the sample passes. In an embodiment, the channel is etched or bored through the solid support or the solid support is otherwise manufactured or assembled to contain a channel. In another embodiment, the channel is continuous (e.g., a loop), to allow continuous cycling in the same direction. In another embodiment, the channel has a vent through which the sample may flow, if desired, for example, to remove the sample or to elute the target molecule.

At least one region of the solid support contains a binding partner immobilized thereon, In an embodiment, the channel contains projections in the sample path. In an embodiment, the projections are staggered. The projections contain at least one immobilized binding partner that binds to the target molecule. When the sample passes through the channel, it bumps into the projections, thereby maximizing exposure of the target molecule to the projections.

In another embodiment, the solid support contains a number of interconnected channels through which the sample flows, which may have immobilized thereto at least one binding partner. In an embodiment, the channels share at least one common portion such that fluid flow is a fluid loop and is cyclical.

The solid support or medium may have several regions containing the same or a different binding partner for at least one target molecule. In an embodiment, the solid support has at least one region that has a binding partner for a non-target molecule immobilized thereon. In another embodiment, the solid support or medium has a number of adjacent regions that contain binding partners for a number of different target and/or non-target molecules. In some embodiments, each of the regions includes binding partners immobilized in that region that differ from the binding partners in each immediately adjacent region. In certain embodiments, there are 5-10, 5-50, 5-100 or more different regions including different target binding partners. In another embodiment, the regions contain different mediums.

In an embodiment, the motive force pushes (e.g., positive pressure) the sample past its binding partner. In another embodiment, the motive force pulls (e.g., negative pressure) the sample past its binding partner. In another embodiment, the magnitude of the motive force is constant during the methods of the invention. In another embodiment, the motive force is provided by a pump. In yet another embodiment, the motive force is an electric current.

In an embodiment, the sample comprises a biological sample, such as stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin.

In an embodiment, the binding partners is a protein, a peptide, a nucleic acid, an amino acid, a nucleoside, an antibody, an antibody fragment, an antibody ligand, an aptamer, a peptide nucleic acid, a small organic molecule, a lipid, a hormone, a drug, an enzyme, an enzyme substrate, an enzyme inhibitor, a coenzyme, an inorganic molecule, a polysaccharide, and a monosaccharide, carbohydrate, or a combination thereof. In a particular embodiment, the binding partner has specificity for at least one human enteric flora nucleotide sequence. In certain embodiments, the binding partner is a target-specific polynucleotide including a nucleotide sequence selected from the group of human nucleotide sequences, human pathogen nucleotide sequences, and human enteric flora nucleotide sequences.

In another embodiment, the methods of the invention includes the step of releasing the target molecule or binding partner. In a particular embodiment, the releasing step includes releasing the target molecule from the first binding partner. In another embodiment, the releasing step includes releasing the first binding partner from the medium.

In a particular embodiment, the invention provides a method for separating target molecules from non-target molecules in a test sample by (a) introducing the test sample to at least a portion of an medium having at least two regions arranged consecutively in a first spatial dimension; (b) subjecting the sample to an electric field in a first direction resulting in migration within the medium of charged molecules through and between the regions in the first spatial dimension; and (c) subjecting the sample to an electric field in a second direction opposite to the first direction, resulting in migration within the medium of charged molecules in the test sample through and between the regions in the first spatial dimension. In these embodiments, at least one of the regions includes a first target binding partners having selective binding affinity for a first target molecule(s) and not having selective binding affinity for non-target molecules. In these embodiments, the first target molecule is selectively bound to the first target binding partner and separated from non-target molecules in the test sample.

In some embodiments, the foregoing methods include the additional step of subjecting the sample to at least one additional cycle of electrophoresis, wherein each cycle includes subjecting the sample to an electric field in the first direction, resulting in migration within the medium of charged molecules in the sample through and between the regions in a first spatial dimension; and subjecting the sample to an electric field in a second direction, resulting in migration within the medium of charged molecules in the sample through and between the regions in the first spatial dimension. In certain embodiments, the methods include subjecting the sample to at least 5, 10, 20, 30 or more such cycles.

In some embodiments, the medium further includes at least one region which is adjacent to at least one of the other regions in a second spatial dimension, e.g., substantially perpendicular to the first spatial dimension, and the method includes the additional step of subjecting the sample to an electric field in a third direction parallel to the second spatial dimension, resulting in migration within the medium of charged molecules in the test sample amongst the regions in the second spatial dimension. In some embodiments, the perpendicular region includes binding partners having selective binding affinity for at least some target or non-target molecules in the sample.

In some embodiments, the medium has a multiplicity of regions arranged consecutively in the first spatial dimension, and each such region includes target binding partners having selective binding affinity for different target molecules and not having selective binding affinity for non-target molecules. In these embodiments, a multiplicity of different target molecules are selectively bound to the multiplicity of target binding partners and separated from non-target molecules in the test sample. In certain embodiments, there are 5-10, 5-50, 5-100 or more different regions including different target binding partners.

In some embodiments, the foregoing methods include the additional step of subjecting the sample to at least one additional cycle of electrophoresis, wherein each cycle includes subjecting the sample to an electric field, resulting in migration within the medium of charged molecules in the sample through and between the regions in the medium in a first direction; and subjecting the medium to a second electric field, resulting in migration within the medium of charged molecules in the sample through and between the regions in a second direction. In an embodiment, the second direction is antiparallel to the first direction. In certain embodiments, the methods include subjecting the sample to at least 5, 10, 20, 30, or more such cycles.

In some embodiments, the medium further includes at least one perpendicular region which is adjacent to at least one of the other regions in a second spatial dimension substantially perpendicular to the first spatial dimension, and the method includes the additional step of subjecting the medium to an electric field in a third direction parallel to the second spatial dimension, resulting in migration within the medium of charged molecules in the sample through and between the regions in the second spatial dimension. In some embodiments, the perpendicular region includes binding partners having selective binding affinity for at least some molecules in the sample.

In another aspect, the invention provides methods of isolating target molecules from non-target molecules in a test sample by separating target molecules from non-target molecules in the test sample by any of the methods described above; releasing the target molecules by treating the medium to release (1) the target molecules or (ii) the target molecules bound to target-specific binding partners; and eluting the released molecules from the medium to isolate the molecules.

In some embodiments, the medium has a second region that includes second target binding partners having selective binding affinity for second target molecules and not having selective binding affinity for non-target molecules. In these embodiments the second target molecules are different from the 'first target molecules, and the second target molecules are selectively bound to the second target binding partners and separated from non-target molecules in the test sample.

In some embodiments, the medium has a multiplicity of regions arranged consecutively in the first spatial dimension, and each such region includes different target binding partners having selective binding affinity for different target molecules and not having selective binding affinity for non-target molecules. In these embodiments, a multiplicity of different target molecules are selectively bound to the multiplicity of target binding partners and separated from non-target molecules in the test sample. In certain embodiments, there are 5-10, 5-50, 5-100 or more different regions including different target binding partners.

In another embodiment, the invention provides methods of detecting target molecules in a dilute or heterogeneous test sample containing non-target molecules by separating, isolating or enriching for the target molecules by the methods described above, amplifying target molecules which are nucleic acids, and/or detecting the target molecules by a method selected from (i) binding of binding partner specific for the target molecules, (ii) binding of a binding partner specific for a complex formed between the target molecules and target-specific binding partners, and (iii) displacement of a detectable ligand from target-specific binding partners by the target molecules.

In certain embodiments, at least one of the regions of the electrophoretic medium includes a volume of beads.

In each of the foregoing aspects and embodiments of the methods, the electrophoretic medium can be selected from the group of acrylamide polymers, agarose polymers, starch polymers, dextran polymers, cellulose polymers and beads. In addition, in each of the foregoing aspects and embodiments, one or more regions of the electrophoretic medium can be formed from different materials than the other region(s) (e.g., different polymeric matrices, different packed beads, or mixtures thereof).

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which.

DETAILED DESCRIPTION

Figure 1:
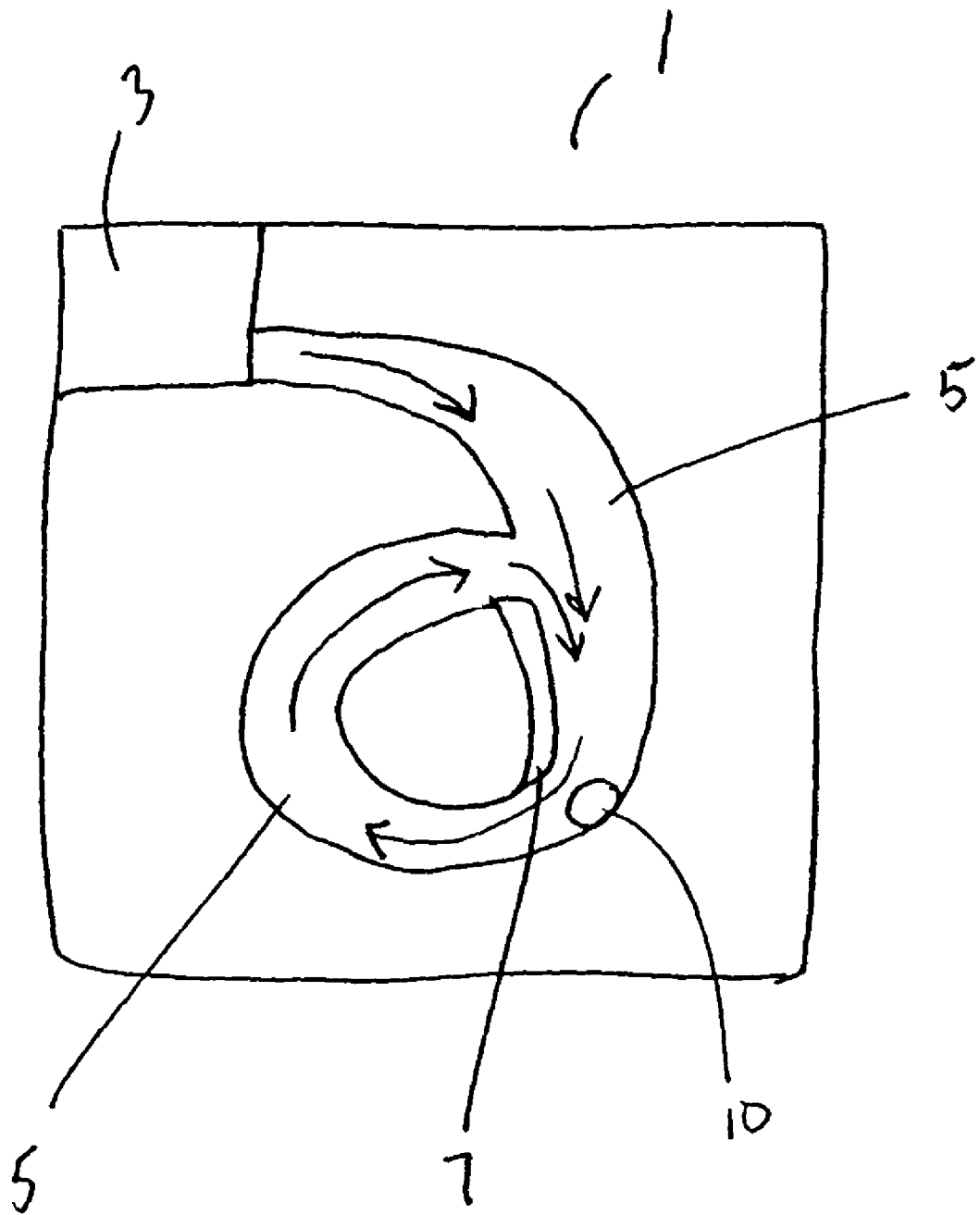
FIG. 1 is a schematic representation of an embodiment of the methods of the invention performed in a solid support having a channel.

All technical and scientific terms used herein, unless otherwise defined below, are intended to have the same meaning as commonly understood by one of ordinary skill in the art. References to techniques employed herein are intended to refer to the techniques as commonly understood in the art, including variations on 'those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "target molecule" means any molecule of interest in a sample that is desired to be detected, separated, isolated, or enriched relative to, non-target molecules within the test sample. Target molecules can include, without limitation, proteins, peptides, nucleic acids, amino acids, nucleosides, antibodies, antibody fragments, antibody ligands, aptamers, peptide nucleic acids, small organic molecules, lipids, hormones, drugs, enzymes, lectin, cell adhesion molecule, antibody epitope, enzyme substrates, enzyme inhibitors, coenzymes, inorganic molecules, polysaccharides, monosaccharides. A sample can include more than one target molecule such that the methods of the invention are used to simultaneously or sequentially separate, isolate, enrich or detect more than one target molecule in a sample. A sample can also include cells expressing target molecules and can be isolated by the methods of the invention.

As used herein, the term "non-target molecule" means any molecule in a sample that is not a target molecule.

As used herein, the term "binding partner" means any molecule which has selective binding affinity for a target molecule or non-target molecule and, therefore, can bind the target molecule during electrophoresis under appropriate conditions (e.g., pH, temperature, solvent, ionic strength, electric field strength). Binding partners can include, without limitation, proteins, peptides, nucleic acids, amino acids, nucleosides, antibodies, antibody fragments, antibody ligands, aptamers, peptide nucleic acids, small organic molecules, lipids, hormones, drugs, enzymes, enzyme substrates, enzyme inhibitors, coenzymes, inorganic molecules, polysaccharides, and monosaccharides.

As used herein, the term "selective binding affinity" means greater affinity for non-covalent physical association or binding to selected molecules relative to other molecules in a sample under appropriate conditions. Examples of selective binding affinity include the binding of polynucleotides to complementary or substantially complementary polynucleotides, antibodies to their cognate epitopes, and receptors to their cognate ligands under appropriate conditions (e.g., pH, temperature, solvent, ionic strength, electric field strength). Selective binding affinity is a relative term dependent upon the conditions under which binding is tested, but is intended to include at least a 2× greater affinity for target molecules than any non-target molecules present in a sample under appropriate conditions. If a test sample includes more than one type of target molecule (e.g., allelic variants from one locus), a binding partner can have selective binding affinity for one or more of the different target molecules relative to non-target molecules.

As used herein, the term "substantially complementary" means having a nucleotide sequence that has sufficient identity to a sequence that is perfectly complementary to a specified polynucleotide to have selective binding affinity for that specified polynucleotide under appropriate conditions.

As used herein, the term "antibody" means any isolated naturally-produced antibody, recombinantly-produced antibody, monoclonal or polyclonal antibody, synthetic antibody such as a chimeric antibody, or any antibody fragment such as an Fab fragment, $F(ab')_2$ fragment, Fv fragment, or single-chain Fv fragment (scFv).

As used herein, the term "aptamer" means any polynucleotide having selective binding affinity for a non-polynucleotide molecule via non-covalent physical interactions. An aptamer is, a polynucleotide that binds to a ligand in a manner analogous to the binding of an antibody to its epitope.

As used herein, the terms "opposite" and "reverse" and "backward", when referring to the direction of electrophoresis, mean a substantially anti-parallel direction relative to a previous direction of electrophoresis. The opposite, reverse or backward direction need not be rotated exactly 180° in the plane of electrophoresis. Rather, a substantially opposite, reverse or backward rotation may be employed (e.g., rotation through 120°-240°) such that the test sample is moved in an oblique manner as in transverse alternating field electrophoresis (TAFE) and contour-clamped homogeneous electric field (CHEF) electrophoresis (see, e.g., Gardiner et al. (1986), *Somatic Cell Molec. Genet.* 12:185-195; Chu et al. (1986), *Science* 234:1582-1585).

As used herein, the terms "detectable" and "labeled" mean chemically constituted or modified to facilitate detection by standard chemical, biochemical, or biological assays including, but not limited to, radioimmunoassay (e.g., radioactive isotope assays), photospectrometric assays (e.g., fluorescence, chemiluminescence, bioluminescence assays), immunoassays (e.g., enzyme-linked immunosorbent assays (ELISA), sandwich assays, immunofluorescence assays, immunoradio assays), hybridization assays (e.g., labeled oligonucleotide hybridization or displacement assays), plasmon resonance assays (e.g., BiaCORE™ assays (Amersham- Pharmacia, Piscataway, N.J.)), nucleic acid amplification assays (e.g., PCR assays, LCR assays), and the like.

As used herein, unless specifically indicated otherwise, the word "or" is used in the inclusive sense of "and/or" and not the exclusive sense of "either/or."

As used herein, the terms "increase" and "decrease" mean, respectively, a statistically significantly (i.e., $p<0.1$) increase or decrease.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geqq 0$ and $\leqq 2$ if the variable is inherently continuous.

Repetitive Affinity Separation

The present invention depends, in part, upon the discovery that the separation, isolation, enrichment or detection of target molecules within a sample is significantly improved by repetitively passing a sample across at least one region of a solid support or through or over at least one region of an electrophoretic medium that has a binding partner specific for the target molecule. In some embodiments, there are two or more regions including binding partners specific for different target molecules. In some embodiments, at least one other region includes a binding partner specific for non-target molecules.

Without being bound to any particular theory of the invention, it is believed that, as the sample moves across a binding partner region multiple times, target molecules within the sample have multiple opportunities to bind to the binding partners specific for the target molecules. Similarly, non-target molecules have multiple opportunities to bind to any binding partners specific for the non-target molecules. In addition, non-specifically bound molecules have additional time and opportunities to be displaced. In an embodiment, the sample is rapidly moved across the binding partner, selecting for only very high specificity binding. Moreover, as a result of the increased opportunities for specific binding, it is believed that that higher stringency binding conditions can be employed to achieve higher specificity without substantial loss of sensitivity. Therefore, the quality of the separation, isolation, enrichment or detection of target molecules is also significantly improved.

The methods are particularly useful for the separation, isolation, enrichment or detection of dilute or heterogeneous samples of biomolecules obtained from bodily fluids, excreta or tissue samples, and can be particularly useful in identifying human wild-type or mutant nucleotide sequences or pathogen-derived nucleotide sequences in stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin.

For example, such methods can be useful in the diagnosis or staging of cancers (e.g., detection of colon cancer-associated nucleic acids or proteins in stool samples), in the diagnosis of infectious disease (e.g., detection of viral proteins in blood samples), in prenatal genotyping (e.g., detection of fetal nucleic acids in amniotic fluid or maternal blood), as well as non-medical applications such as environmental testing (e.g., detection of pathogens in water supplies) and industrial or commercial process controls (e.g., meat and poultry processing; food and pharmaceutical processing).

Furthermore, the methods are particularly useful for separating, isolating, enriching or detecting multiple targets in a single sample. For example, a genomic DNA, mRNA, cDNA or amplified DNA sample can be screened for the presence a multiplicity of mutant or marker DNA sequences simultaneously, or an environmental sample can be screened for the presence of a multiplicity of pathogens simultaneously.

In one aspect, the present invention provides a cartridge for use in methods for separating target molecules from non-target molecules in a sample. By way of example and as illustrated in, FIG. 1, the cartridge 1 has a substantially planar housing, fabricated from a moldable material such as polystyrene or polycarbonate, or polyvinylchloride, defining at least one fluid inlet port 3 and at least one conduit 5 having a fluid contacting surface in fluid communication with the fluid inlet port 3. The cartridge I further comprises at least one binding partner disposed on a first region 7 of the fluid contacting surface of the conduit 5, so that when a sample is applied to the fluid inlet port 3, the sample traverses the region and target molecules in the sample bind to the binding partner during transport of the sample through the conduit 5. FIG. 1 illustrates an embodiment of the cartridge in which the conduit forms a loop through which the sample can repeatedly pass, thereby repeatedly contacting the binding partner for the target molecule. In an embodiment, at least one region comprises a binding partner for a non-target molecule. The cartridge may also comprise at least one additional port or vent 10 that attaches to a pump for circulating the sample or through which the sample can be removed or through which the target molecule can be eluted. Elution of the molecules bound to the binding partners in individual regions of the conduit may be performed separately such that several target molecules and/or non-target molecules are separated and/or isolated. In an embodiment, the regions of the cartridge can be separated (e.g., snapped apart) prior to the Elution step. In another embodiment, the regions of the cartridge can be isolated such that fluid communication is no longer possible between the regions and molecules bound in each region can be eluted and isolated separately.

Figure 2:
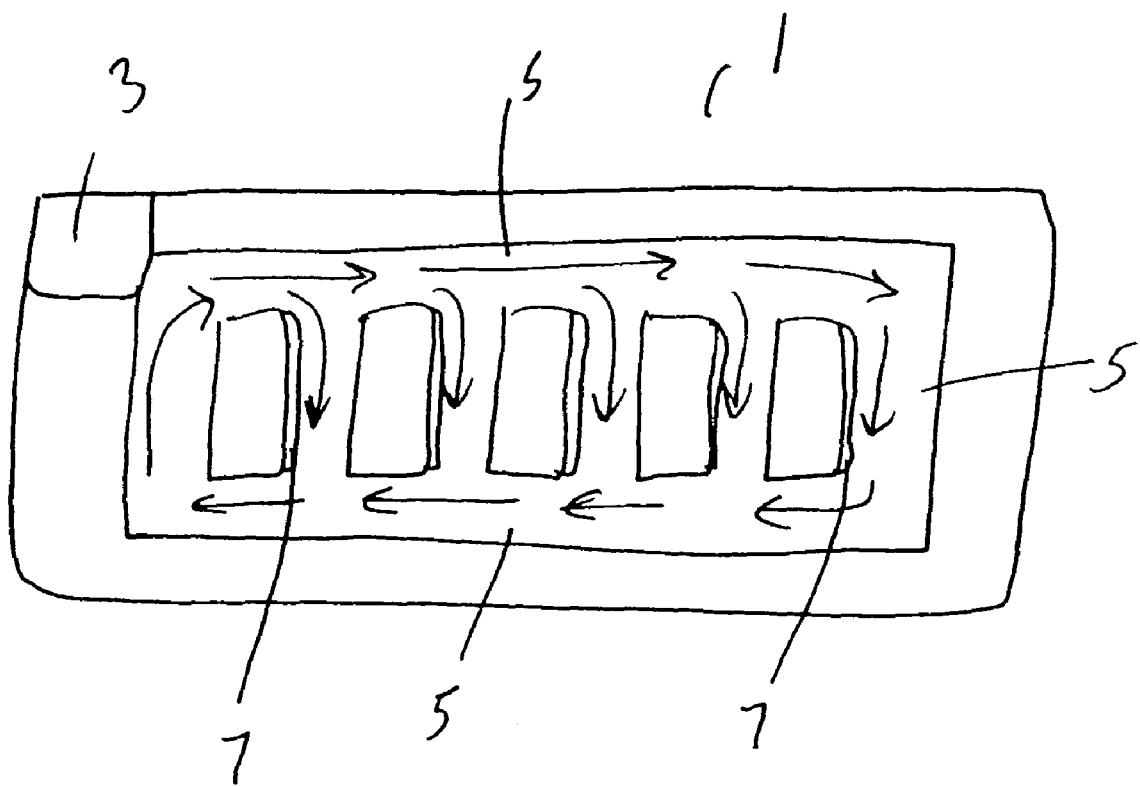
FIG. 2 is a schematic representation of an embodiment of the methods of the invention performed in a solid support having a plurality of channels.

Referring to FIG. 2, in another embodiment, the cartridge 1 comprises a fluid inlet port 3 and multiple conduits 5 in fluid communication with each other and at least one region 7 of the conduits contains a binding partner for a target molecule. The a sample can traverse the conduits and the target molecule binds to its binding partner, which are bound to regions of the conduits. Multiple conduits are useful for increasing the surface area to which binding partners for target molecules are bound or for having several regions containing different binding partners for different target molecules and/or non-target molecules. In an embodiment, at least one region contains a non-target molecule. The cartridge may also have at least one additional port or vent for attaching to a pump or through which the sample can be removed or through which the target molecule can be eluted. Elution of the molecules bound to the binding partners in individuals regions may be performed separately such that several target molecules and/or non-target molecules are separated and/or isolated. In an embodiment, the regions or conduits of the cartridge can be separated (e.g., snapped apart) prior to the elution step. In another embodiment, the regions of the cartridge' can be isolated such that fluid communication is no longer possible between the conduits or regions and molecules bound in each region can be eluted and isolated separately.

Figure 3:
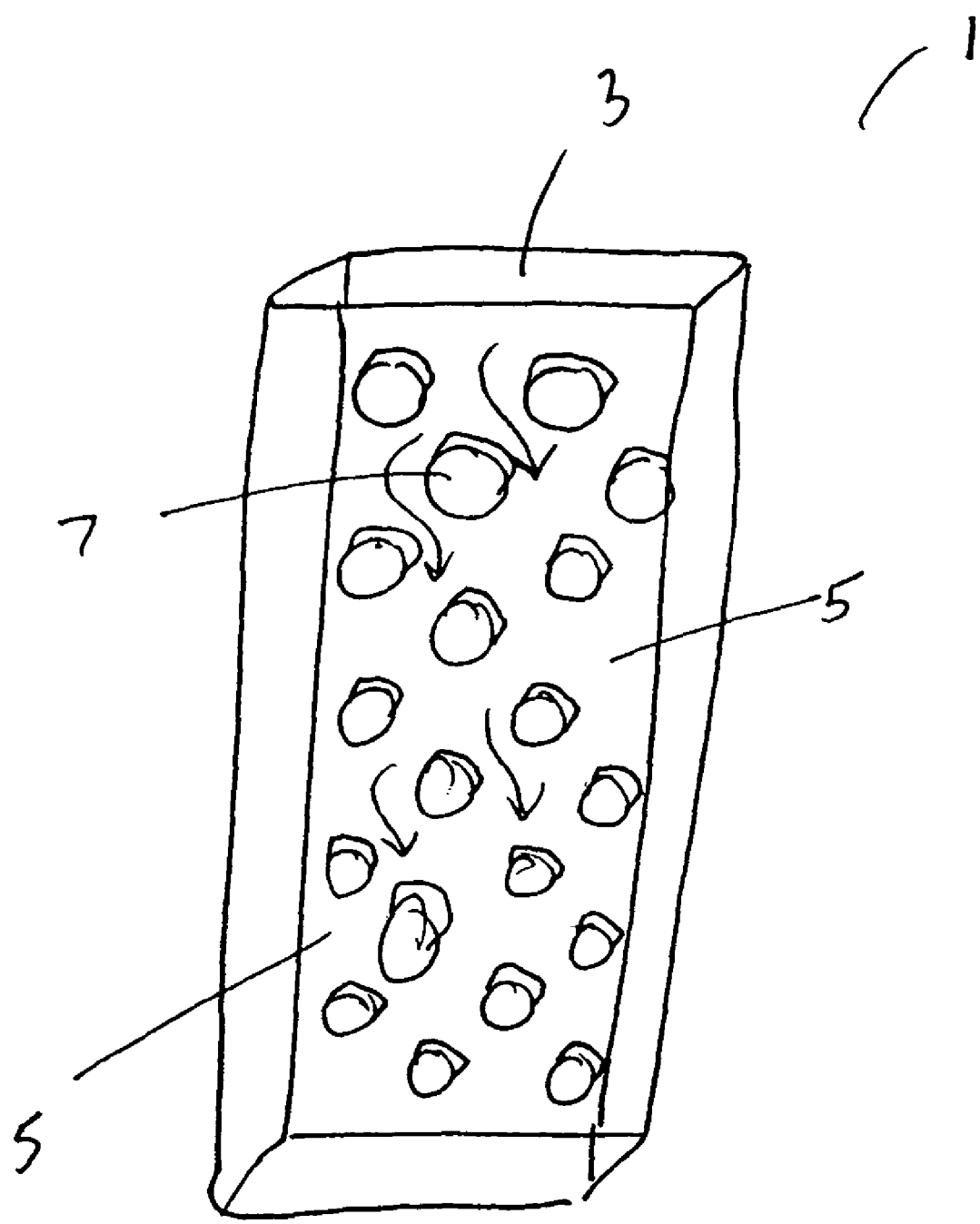
FIG. 3 is a cross section of a solid support used in the practice of the methods of the invention.
Figure 4:
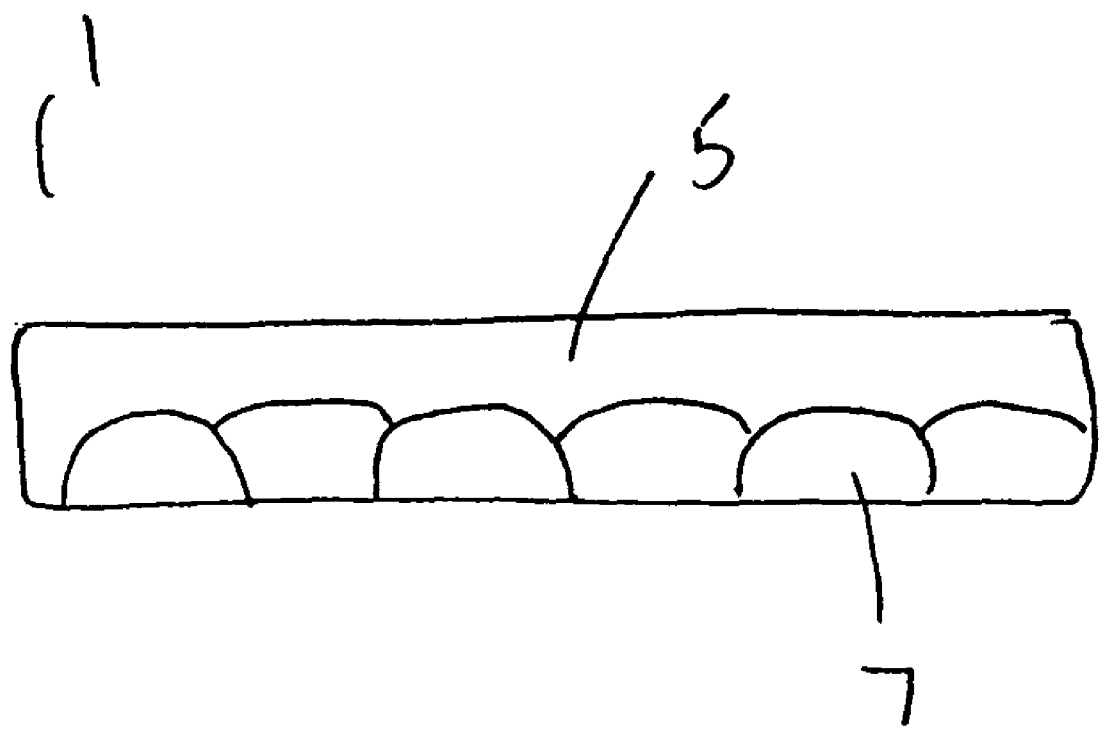
FIG. 4 is a schematic representation of the cross-section shown in FIG. 3.

Referring to FIG. 3, in another embodiment, the cartridge 1 comprises a fluid inlet port 3 and at least one conduit 5 in fluid communication with the fluid inlet port 3 and at least one region of the conduit that comprises at least one projection 7 containing a binding partner for a target molecule. Projections protrude into the conduit such that target molecules flows into and around the projection and provide additional surface' area for binding partners for target molecules, thereby' increasing the opportunity of the target molecule to bind to its binding• 'partner. In an embodiment, the projections are staggered as shown in FIG. 3. The projection may be any shape, e.g., may be rounded, flat, or square, for example. FIG. 4 illustrates a cross section of an embodiment of the embodiment of FIG. 3, showing the projections 7 with in the conduit 5. In an embodiment, for example, the sample can be pulled along the conduit to via positive or negative pressure induced by a pump connected to a pump port located up stream or downstream of the region containing the binding partner. The pumps may be alternated such that the sample passes back and forth over the binding partner region. Alternatively, a manual system may be used, such as, for example, two syringes attached to either end of the cartridge, in which the sample is repeatedly pulled or pushed past the regions of the conduit comprising the binding partner, using positive or negative pressure of the syringes. Fluid flow through the cartridge is achieved, for example, by the methods described, in U.S. Pat. No. 6,287,850.

In an embodiment of the invention the cartridge is a microchip or wafer, and binding partner arrays are prepared, for example, as described in U.S. Pat. No. 5,143,854 or PCT WO 92/10092. The chip may be composed of a wide range of material, either biological, nonbiological, organic, inorganic, or a combination of any of these, existing as particles, strands, precipitates, gels, sheets, tubing, spheres, containers, capillaries, pads, slices, films, plates, slides, etc. The chip may have any convenient shape, such as a disc, square, sphere, circle, etc. The chip is preferably flat but may take on a variety of alternative surface configurations. For example, the chip may contain raised or depressed regions on which a binding partner is located. The chip and its surface preferably form a rigid support on which the binding partner can be formed. The chip may be a polymerized Langmuir Blodgett film, functionalized glass, Si, Qe, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other materials with which the chip can be composed of will be readily apparent to those skilled in the art upon review of this disclosure as well as U.S. Pat. Nos. 6,287,850, 6,399,365, 6,551,817, 6,664,104, 6,653,121, and 6,664,104, the entire disclosures of which are incorporated herein by reference. In a preferred embodiment, the chip is flat glass or single-crystal silicon, The surface of conduit within the chip maybe composed of the same material as the wafer and may be composed of any of a wide variety of materials, for example, polymers, plastics, resins, polysaccharides, silica or silica-based materials, carbon, metals, inorganic glasses, membranes, or any of the above-listed wafer materials.

In another aspect, the invention provides methods of preparing the cartridge by drying a binding partner onto the surface of at least a portion of one conduit of the cartridge. Drying of the binding partner is accomplished by applying a volume of a mixture comprising a binding partner of interest onto the surface of at least a portion of at least one conduit. The binding partner used will depend upon what the cartridge will be used to assay for. The binding partner may be permanently bound to the conduit or may be reversibly bound to the conduit according to art known methods.

Repetitive Reverse-Field Affinity Electrophoresis

In an embodiment, the present invention provides methods for separating target molecules from non-target molecules in a test sample by subjecting the sample to repetitive reversed-field affinity electrophoresis in an electrophoretic medium having at least two regions arranged consecutively, e.g., in a first spatial dimension. At least one of the regions includes a first binding partner having selective binding affinity for a first target molecule and not having selective binding affinity the non-target molecules. The electrophoretic medium is first subjected to an electric field in a first direction resulting in migration within the medium of charged molecules amongst the regions in the first spatial dimension. The electric field is then reversed such that the electrophoretic medium is subjected an electric field in a second direction substantially antiparallel to the first direction, resulting in migration within the medium of charged molecules in the test sample amongst the regions in the first spatial dimension. This process of reversing the electric field and electrophoresing the sample in the opposite direction can be repeated one or more times. For example, the test sample can be subjected to 5, 10, 20, 30 or more cycles of reversed-field electrophoresis in which the sample is electrophoresed in one direction and then the opposite direction. In an embodiment, the first and second electrophoretic fields comprise between about 1 Amps to about 200 Amps, depending upon the electrophoretic medium used (e.g., concentration of agarose or polyacrylamide, pH, temperature) and size of the molecule or cell being separated or isolated. In another embodiment, the first and second electrophoretic fields cause the target molecule to move through the medium at a rate of between about 1 mm/mm. to about 100 cm/mm.

Figure 5:
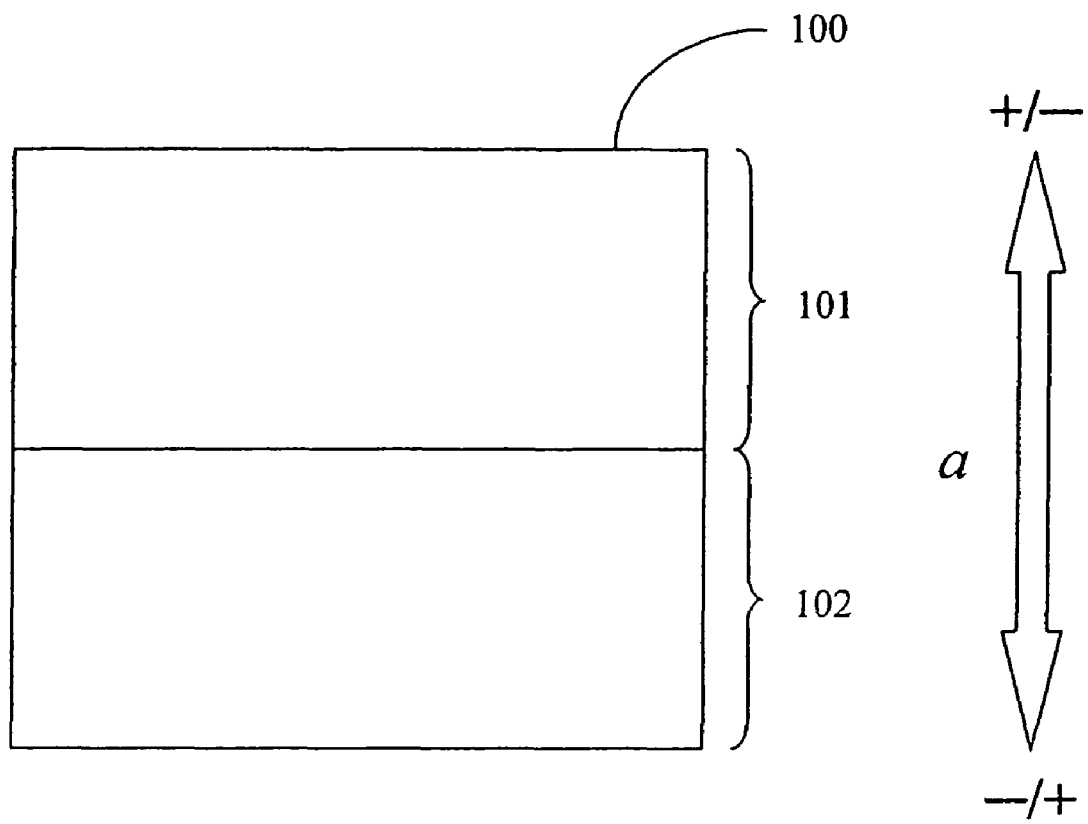
FIG. 5 is a schematic representation of an electrophoretic device of the invention having an electrophoretic medium with two regions.

FIG. 5 is a schematic representation of an electrophoretic device of the invention having an electrophoretic medium 100 with a first region 101 and a second region 102. In the foregoing embodiments, one region includes immobilized target-specific binding partners and the other does not. These regions are arranged in a first spatial dimension indicated by arrow a. The test sample is applied or introduced to one or both regions, typically to the distal edge of one region, and is then subjected to an electric field in dimension a such that charged molecules migrate amongst the regions. The electric field is then reversed such that charged molecules migrate amongst the regions in the opposite direction in dimension a. In accordance with the invention, the electric field can be reversed and the test sample can be electrophoresed forward and backward multiple times in spatial dimension a to achieve improved separation. The regions need not be of equal size as shown in the schematic representation of FIG. 5, and the shapes of the regions can be arbitrary. Furthermore, the binding partners need not be evenly distributed within a region.

Figure 6:
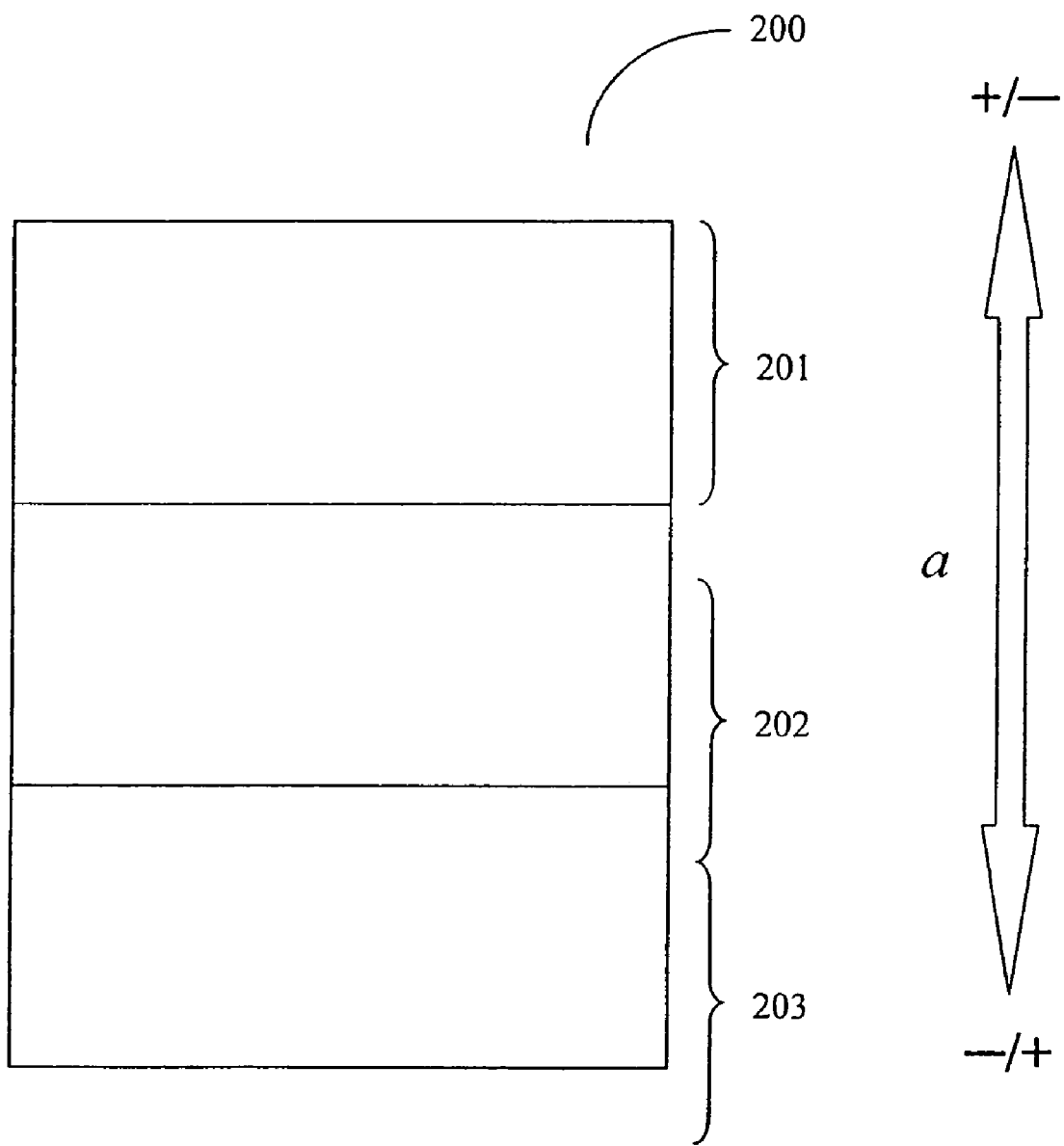
FIG. 6 is a schematic representation, of an electrophoretic device of the invention having an electrophoretic medium with three regions.

FIG. 6 is a schematic representation of an electrophoretic device of the invention having an electrophoretic medium 200 with a first region 201, a second region 202 and a third region 203. In the foregoing embodiments, one region (e.g., the second region 202) includes immobilized target-specific binding partners. These regions are arranged in a first spatial dimension indicated by arrow a. The test sample is applied or introduced to one or more regions, typically to the distal edge of region 201 or 203, and is then subjected to an electric field in spatial dimension a such that charged molecules migrate amongst the regions. The electric field is then reversed such that charged molecules migrate amongst the regions in the opposite direction in spatial dimension a. In accordance with the invention, the electric field can be reversed and the test sample can be electrophoresed back-and-forth multiple times in spatial dimension a to achieve improved separation.

In some embodiments, the electrophoretic medium has a second region that includes second target binding partners having selective binding affinity for second target molecules and not having selective binding affinity for non-target molecules. In these embodiments the second target molecules are different from the first target molecules, and the second target molecules are selectively bound to the second target binding partners and separated from non-target molecules in the test sample.

Referring again to FIG. 7, an electrophoretic device of the invention has an electrophoretic medium 100 with a first region 101 and a second region 102, arranged in a first spatial dimension indicated by arrow a. In these embodiments, the first region 101 includes first target binding partners and the second region 102 includes second target binding partners. Similarly, referring again to FIG. 6, an electrophoretic device of the invention has an electrophoretic medium 200 with a first region 201, a second region 202 and a third region 203, arranged in a first spatial dimension indicated by arrow a. In these embodiments, two regions e.g., the first region 201 and second region 202) include first and second target binding partners. As before, the test sample is applied or introduced to one or more of the regions, and is subjected to repetitive reversed-field electrophoresis in dimension ∀.

In other embodiments, the electrophoretic medium has a multiplicity of regions arranged consecutively in the first spatial dimension, and each such region includes different target binding partners having selective binding affinity for different target molecules and not having selective binding affinity for non-target molecules. In these embodiments, a multiplicity of different target molecules are selectively bound to the multiplicity of target binding partners and separated from non-target molecules in the test sample. In certain embodiments, there are 5-10, 5-50, 5-100 or more different regions including different target binding partners.

In another embodiment, an electrophoretic device of the invention has an electrophoretic medium with a first region, a second region, a third region and a fourth region. A multiplicity of regions include immobilized target-specific binding partners. Optionally, one or more regions that does not include target-specific binding partners does include non-target-specific binding partners. The regions are arranged in a first spatial dimension. As before, the test sample is applied or introduced to one or more of the regions, and is subjected to repetitive reversed-field electrophoresis in a dimension.

In another aspect, the present invention provides methods employing both target-specific and non-target-specific binding partners. In these embodiments, at least one of the regions arranged in the first spatial dimension of the electrophoretic medium includes target binding partners having selective binding affinity for target molecules and not having selective binding affinity for non-target molecules, and at least one of the regions includes non-target binding partners having selective binding affinity for at least some non-target molecules and not having selective binding affinity for target molecules. The region including the non-target-specific binding partners is useful for removing at least some non-target molecules from the electrophoretically migrating sample, thereby eliminating some non-target molecules which might non-specifically bind to target-specific binding partners or otherwise interfere with the binding of target molecules to target-specific binding partners. As in the previously described embodiments, the test sample is applied or introduced to one or more of the regions, and is subjected to repetitive reversed-field electrophoresis in the first spatial dimension.

Referring again to FIG. 5, an electrophoretic device of the invention has an electrophoretic medium 100 with a first region 101 and a second region 102, arranged in a first spatial dimension indicated by arrow a. In these embodiments, the first region 101 includes target-specific target binding partners and the second region 102 includes non-target-specific binding partners. Similarly, referring again to FIG. 6, an electrophoretic device of the invention has an electrophoretic medium 200 with a first region 201, a second region 202 and a third region 203, arranged in a first spatial dimension indicated by arrow a. In these embodiments, at least one region includes target-specific binding partners (e.g., the second region 202) and at least one region includes non-target-specific binding partners (e.g., the first region 201 and/or the third region 203). Similarly, in one embodiment, an electrophoretic device of the invention has an electrophoretic medium with a first region, a second region, a third region, and a fourth region, arranged in a first spatial dimension. In these embodiments, at least one region includes target-specific binding partners (e.g., the second region and the third region) and at least one region includes non-target-specific binding partners (e.g., the first region and/or the fourth region). As before, the test sample is applied or introduced to one or more of the regions, and is subjected to repetitive reversed-field electrophoresis in a dimension.

In some embodiments of each of the foregoing aspects, the electrophoretic medium further includes at least one perpendicular region which is adjacent to at least one of the other regions in a second spatial dimension substantially perpendicular to the first spatial dimension. In these embodiments, the method includes the additional step of subjecting the electrophoretic medium to an electric field in a third direction parallel to the second spatial dimension, resulting in migration within the electrophoretic medium of charged molecules in the test sample amongst the regions in the second spatial dimension. Thus, the invention provides for separation in a second spatial dimension. In some embodiments, the perpendicular region includes binding partners having selective binding affinity for at least some molecules in the sample. In accordance with the invention, the electric field in the second spatial dimension optionally can be reversed and the test sample can be electrophoresed back-and-forth multiple times in the second spatial dimension to achieve improved separation. Electrophoresis in the second spatial dimension can be performed before, after or alternately with electrophoresis in the first spatial dimension, In some embodiments, electrophoresis in the second spatial dimension is performed only once, without field-reversal, to achieve a final separation prior to isolation or detection of the target molecules.

Figure 7:
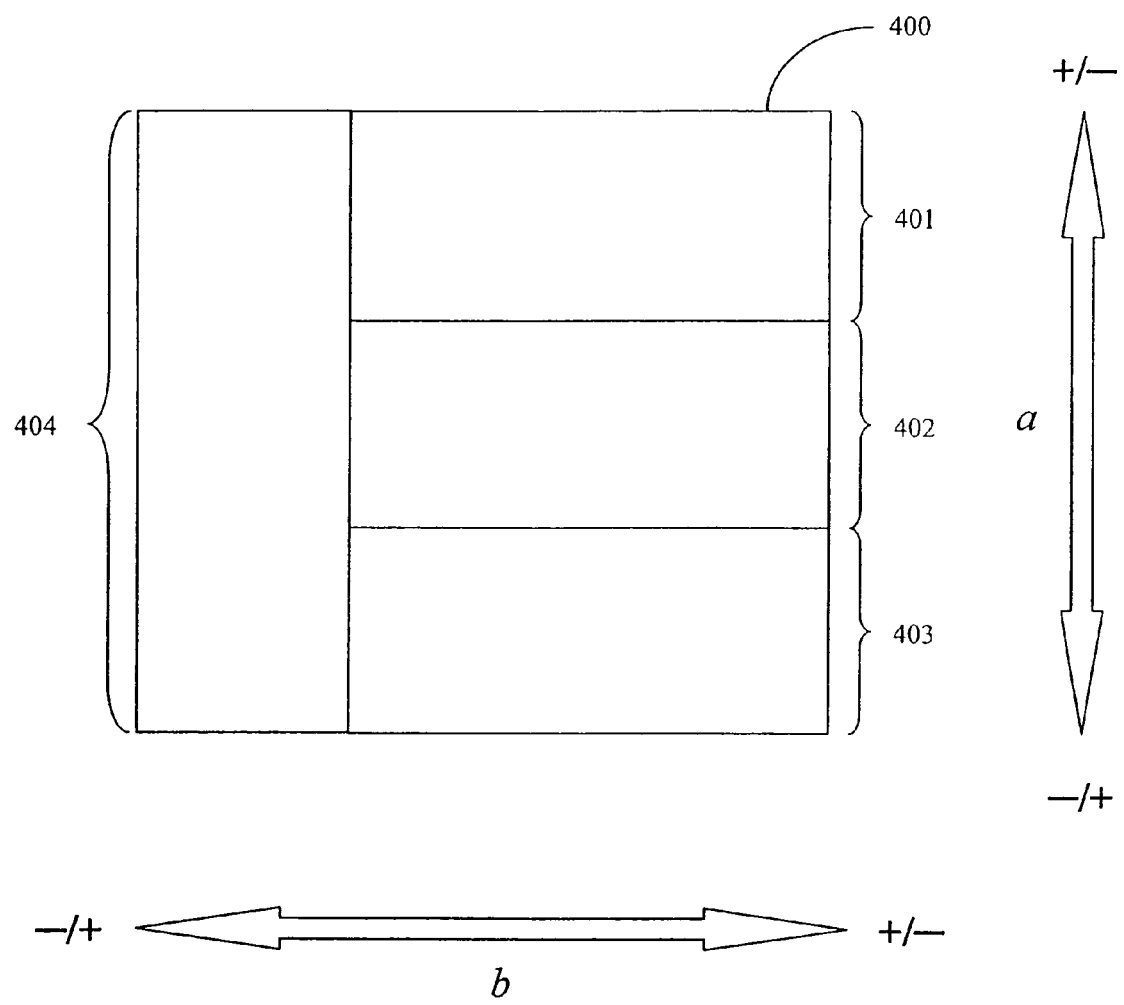
FIG. 7 is a schematic representation of an electrophoretic device of the invention having an electrophoretic medium with four regions arranged in two spatial dimensions.

FIG. 7 is a schematic representation of an electrophoretic device of the invention having an electrophoretic medium 400 with a first region 401, a second region 402, and a third region 403 arranged in a first spatial dimension indicated by arrow a~ A perpendicular region 404 is arranged in a second spatial dimension indicated by arrow b relative to the other regions. At least one of regions 401, 402 and 403 includes immobilized target-specific binding partners. Optionally, one or more of regions 401, 402 and 403 which does not include target-specific binding partners can include non-target-specific binding partners. The perpendicular region 404 can optionally include target-specific or non-target-specific binding partners. The test sample is applied or introduced to one or more regions, typically to the distal edge of region 401 or 403, and is then subjected to an electric field in spatial dimension a such that charged molecules migrate amongst regions 401, 402 and 403. The electric field is then reversed such that charged molecules migrate amongst these regions in the opposite direction in spatial dimension a. In accordance with the invention, the electric field can be reversed and the test sample can be electrophoresed back-and-forth multiple times in spatial dimension a to achieve improved separation. The test sample is also subjected to an electric field in spatial dimension b such that charged molecules migrate amongst regions 401, 402 and 403 and perpendicular region 404. The electric field can be reversed and the sample can be electrophoresed back-and-forth multiple times in spatial dimension b, or electrophoresis in dimension b can be performed only once, without field-reversal, to achieve a final separation prior to isolation or detection of the target molecules. Although three regions (i.e., 401, 402 and 403) are shown in spatial dimension, an arbitrary number of regions can be included. Similarly, additional regions can be included in spatial dimension b.

In another aspect, the invention provides methods of isolating target molecules (e.g. nucleic acids) from non-target molecules in a test sample. In these methods, the target molecules are separated by any of the methods described above, and then the target molecules are released by treating the electrophoretic medium to release either the target molecules from target-specific binding partners, or to release complexes of the target molecules and target-specific binding partners. These released molecules are then eluted from the electrophoretic medium to isolate the target molecules. The treatment for releasing the molecules depends upon the nature of the molecules to be released. For example, and without limitation, heat, salts, denaturants, or increased electric fields can be used to release polypeptides or proteins bound to polypeptide, protein or aptamer binding partners, or to dissociate nucleic acid targets hybridized to complementary or substantially complementary polynucleotide binding partners. Similarly, and without limitation, chemical cleavage, enzymatic cleavage, or mechanical cleavage (e.g., cutting the binding region from the medium), as well as heat, salts, denaturants, or increased electric fields, can be used to release complexes of immobilized binding partners and bound target molecules from the medium.

In another aspect, the invention provides methods of enriching for target molecules (e.g., specific nucleic acids) relative to non-target molecules in a test sample. In these methods, the target molecules are separated and released by any of the methods described above, and then the target molecules are eluted from the electrophoretic medium to provide a sample enriched for the target molecules.

In another aspect, the invention provides methods of detecting target molecules (e.g., specific nucleic acids) in a test sample containing non-target molecules. In these methods, the target molecules are separated by any of the methods described above, optionally isolating or enriching for the target molecules by the methods described above, and then the target molecules are detected by any appropriate method of detection. For example, and without limitation, polypeptide target molecules can be detected by binding of a detectable antibody, aptamer, receptor or ligand specific for the target polypeptide, and nucleic acid target molecules can be detected by binding of a polynucleotide probe specific for the target nucleic acid, or by displacement of a detectable polynucleotide hybridized to target-specific binding partners by the target nucleic acids. Optionally, target molecules which are nucleic acids can be amplified prior to detection.

In some of the foregoing embodiments, the adjacent regions of the electrophoretic medium are contiguous such that the regions form a single continuous electrophoretic medium. In other embodiments, the regions are not contiguous but, rather, are separated either by a solvent-filled void, spacer, separator, or other structure(s) such that the regions form a discontinuous electrophoretic medium in which the regions are in fluid communication. In embodiments employing packed volumes of beads in one or more regions of the electrophoretic medium, separators can prevent beads from migrating amongst regions in response to an electric field.

In some of the foregoing embodiments, the invention is employed with highly heterogeneous or complex test samples in which the target molecules comprises a very small fraction of the biomolecules present. In some of these embodiments, it is contemplated that the invention can employ (a) a greater number of non-target specific binding partners relative to target-specific binding partners to capture the greater relative number of non-target molecules, (b) a variety of non-target specific binding partners to capture a variety of non-target molecules, and/or (c) non-target specific binding partners with less specificity or selectivity relative to target-specific binding partners such that each non-target specific binding partner can capture a variety of different non-target molecules (e.g., under a given set of conditions, longer polynucleotide probes can hybridize with lower specificity than shorter probes).

In some of the foregoing embodiments, the adjacent regions of the electrophoretic medium are identical except for the differing binding partners immobilized within the different regions. In other embodiments, the regions can differ in the chemical composition of the medium such that characteristics such as pore size, denaturant composition and/or concentration, ionic charge, pH, salt concentration, or hydrophobicity/hydrophilicity are varied. Such variables can be used to separate molecules based upon physical size in native or denatured conformations, net charge at different pH values, binding affinity for binding partners at different binding (e.g., hybridization) stringencies, or non-specific binding affinity for the electrophoretic medium itself. These characteristics can also be varied within a region over time by varying the electrophoresis solvent or otherwise treating the region. Finally, the temperature of the electrophoretic medium and the strength of the electric field can be varied over time, thereby affecting the binding characteristics of the binding partners immobilized within the different regions of the electrophoretic medium.

It is understood by those of skill in the art that the separation, isolation or enrichment of a target molecule in a sample need not be complete for most analytical or diagnostic purposes. Rather, varying degrees of separation, isolation or enrichment have utility for varying purposes. Therefore, the terms "separation", "isolation" or "enrichment" are intended to have their usual meaning in the art, conveying a statistically significant increase in separation, isolation or enrichment and not an absolute separation of all target molecules from all non-target molecules.

Electrophoretic Media

Electrophoretic media useful in the invention include any media through which charged molecules can migrate in solution in response to an electric field and to which binding partners can be immobilized, including polymeric matrices of gels, packed volumes of particles or beads, and hybrid media including beads or particles embedded in a polymeric gel matrix.

In some embodiments, one or more regions of the electrophoretic medium can be formed from different materials than the other regions (e.g., different polymeric matrices, different packed beads, hybrid gel-bead media, and combinations thereof). The materials for the different regions can be selected according to principles well known in the art to effect different separations or to selectively retain target or non-target molecules.

A. Polymeric Gel Media.

In some embodiments, one or more of the regions of the electrophoretic medium are formed as a polymeric gel. Commonly used gel media useful in the invention include polymeric gels formed from monomers of acrylamide, agarose, starches, dextrans, and celluloses, as well as chemically modified or functionalized variants of these monomers (see, e.g., Polysciences, Inc., Polymer & Monomer catalog, 1996-1997, Warrington, Pa.), (Smithies (1959), *Biochem. J.* 71:585; Quesada (1997), *Curr. Opin. Biotech.* 8:82-93).

For the separation of proteins, 5-15% (w/v) polyacrylamide gels are typically used. For small nucleic acid molecules (e.g., <1 kb), 5%-20% (w/v) polyacrylamide gels can be used. For the separation of very large nucleic acid fragments, however, the pore size of standard polyacrylamide gels can be insufficient to allow adequate movement and separation of the fragments. Therefore, lower percentage polyacrylamide gels (e.g., 2-5% (w/v)) can be used. These low percentage polyacrylamide gels, however, have poor mechanical strength. Alternatively, agarose electrophoretic media can be used for nucleic acid gels. For example, gels of 0.5-2.0% (w/v) agarose can be for most nucleic acid separations, and 0.5-1.0% (w/v) gels can be used for larger nucleic acid fragments. Low percentage agarose gels have greater mechanical strength than low percentage polyacrylamide gels.

For some methods, composite gel media containing a mixture of two or more supporting materials can be used, For example, and without limitation, composite acrylamide-agarose gels can be employed which contain from 2-5% (w/v) acrylamide and 0.5%-1.0% (wfv) agarose. In such gels, the polyacrylamide matrix performs provides the major sieving function, whereas the agarose provides mechanical strength for convenient handling without significantly altering the sieving properties of the acrylamide. In composite gels, the binding partners optionally can be attached to the component that performs the major sieving function of the gel, because that component more intimately contacts the target molecules.

In other embodiments, macroporous gels can be formed by mixing the gel-forming materials with organic liquids or pore-forming agents prior to polymerization. These liquids or pore-forming agents can be removed subsequent to polymerization to create a polymeric gel matrix with larger pores. The larger pores are useful for permitting the movement of large target molecules (e.g., genomic fragments) through the polymeric matrix material, while also maintaining the mechanical strength of the medium.

B. Packed Bead Media.

In other embodiments, as an alternative to polymeric gel media, packed volumes of small beads or particle beds can be used as electrophoretic media. Such particle beds, which are frequently used in chromatography, have the advantage of large interstitial voids which allow for the passage of large molecules such as nucleic acid fragments>1 kb. In some embodiments, the beads have average diameters in the range of 1-5: m, 5-50: m, or 50-150: m, although larger beads can also be used. Beads useful in the invention can be formed from materials including, but not limited to, agarose polymers, dextran polymers, acrylic polymers, glass, latex, polystyrene, poly(hydroxyethylcellulose), poly(ethylenoxide), a modified acrylamide, and acrylate ester.

Beads useful in the invention can be solid beads or porous beads, In some embodiments, porous beads will have diameters in the range of 10-20: m or, more generally 10-50: m, and can have a wide range of pore sizes. Such porous beads can include binding partners embedded within the pores and/or bound to the surfaces of the probes. Non-porous or solid beads can have a wider range of diameters, including without limitation beads in the range of 1-100: m.

Such beads conveniently can be coated (including the interiors of pores) with one member of an affinity binding pair such that binding partners bound to the other member of the affinity binding pair can be immobilized on the beads. For example, and without limitation, beads can be coated with avidin or streptavidin and binding partners can be conjugated to biotin to cause immobilization of the binding partners on the beads. Similarly, probes can be coated with Protein A to immobilize antibody binding partners that bind to Protein A.

Beads also can be treated or coated to reduce non-specific binding or target or other molecules in a sample. For example, beads can be treated to reduce the number of hydrophobic groups (e.g., benzyl groups) on the surface, or to increase the number of hydrophilic groups (e.g., carboxyl groups) on the surface. Beads can also be coated with gelatin, bovine serum albumin or other molecules that will non-specifically bind to and "block" the surface prior to use with test samples.

In embodiments employing beads as electrophoretic media, it may be necessary to separate different regions of the electrophoretic medium by separators which are membranes or meshes that prevent the movement of the beads from one region to another in response to the electric field. Such separators must have pores sufficiently large to be permeable to the target molecules, but not permeable to the beads. Such separators can be used alone, or in combination with spacer elements or other structures between regions of the electrophoretic medium.

C. Hybrid Gel-Bead Media.

In other embodiments, hybrid media can be formed which include small beads or particles embedded or enmeshed in a polymeric gel. Such hybrid-gel media can be formed from any of the polymeric gel materials and any of the bead materials described above. For example, and without limitation, polyacrylate or polystyrene beads can be embedded in a polyacrylamide or agarose gel matrix. In some embodiments, the binding partners will be bound to the beads prior to production of the hybrid gel-bead media. In other embodiments, however, the binding partners can be co-polymerized into the polymeric gel during its formation, or can be bound to the hybrid gel-bead media after formation.

D. Electrophoretic Conditions.

Appropriate conditions for electrophoresis, including buffer systems, temperature, and voltage, can be chosen by those of skill in the art, according to well known principles, depending upon the type of test sample and target molecules being assayed and the type of electrophoretic medium being employed.

For example, because the target molecules must be charged in order to migrate in an electric field, buffers of suitable pH are chosen such that the target molecules are appropriately charged during electrophoresis. In some embodiments, the buffers can be varied during or between electrophoretic steps or cycles in order to alter the charges of the target or non-target molecules and thereby affect electrophoretic separation. In addition, buffers can be chosen which promote greater or lesser degrees of stringency or selectivity of affinity binding to the binding partners. For example, when attempting to capture all alleles of a given gene with a single polynucleotide binding partner, a lesser degree of stringency can be employed than when attempting to capture only a specific allele which differs from other alleles by a single nucleotide polymorphism.

Similarly, the electrophoretic medium can be maintained at a chosen temperature to prevent denaturation of biomolecules (e.g., <37° C.) or to promote denaturation (e.g., 60° C.-90° C.). In some embodiments, the temperature can be varied during or between electrophoretic steps or cycles in order to alter the binding of the target or non-target molecules and thereby affect electrophoretic separation. For example, when attempting to capture all alleles of a given gene with a single polynucleotide binding partner, a lower temperature can be employed than when attempting to capture only a specific allele which differs from other alleles by a single nucleotide polymorphism.

Similarly, the electric field across an electrophoretic medium can be chosen according to principles well known in the art. In particular, voltages are chosen which cause a current which allows the target molecules to migrate amongst regions in a reasonable period of time without causing substantial temperature increases in the medium which might disrupt either the target molecules or the medium itself. Typically, for protein electrophoresis in an SDS-polyacrylamide gel, currents of 2-20 mA can be used, whereas for agarose gel electrophoresis of nucleic acids, a current of 100-200 mA can be used.

Target Molecules and Test Samples

The target molecules to be separated, isolated, enriched or detected by the methods of the present invention include any charged biomolecules which are capable of separation by electrophoresis in an appropriate buffer. Such target molecules include, without limitation, nucleic acids, such as genomic DNA, cDNA, mRNA or amplified DNA/RNA products, small polypeptides such as certain hormones and proteolytic fragments, and larger polypeptides such as secreted proteins, structural proteins, receptors, enzymes, amino acids, nucleosides, antibodies, antibody fragments, antibody ligands, aptamers, peptide nucleic acids, small organic molecules, lipids, hormones, drugs, enzymes, enzyme substrates, enzyme inhibitors, coenzymes, inorganic molecules, polysaccharides, monosaccharides. In addition, the target molecules can be specific allelic variants of these molecules, such as mutant or disease-associated forms, or allelic variants which are useful in forensic identifications. In some embodiments, there will be a single type of target molecule (e.g., a nucleic acid having a specific nucleotide sequence), whereas in other embodiments the target molecules can comprise a class of molecules (e.g., nucleic acids of varying lengths including a specific nucleotide sequence, or nucleic acids corresponding to various alleles of a particular gene).

Test samples which can be used in the present invention include any samples which include target biomolecules which can be separated, isolated, enriched or detected by the methods of the invention. Such test samples include, without limitation, bodily fluids, excreta and tissue samples. For example, stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, a nucleated cell sample, a fluid associated with a mucosal surface, hair, or skin can all be used as sources for test samples. In addition, test samples for environmental testing (e.g., detection of pathogens in water supplies) and industrial or commercial process controls (e.g., meat and poultry processing) can be used. For example, and without limitation, test samples can be obtained from ponds, streams or rivers, watersheds, municipal water supplies, water treatment facilities, meat and poultry slaughterhouses or processing plants, food processing factories, pharmaceutical and biologics manufacturing facilities, blood banks, organ banks and the like. Test samples can also be obtained from sites of potential contamination with dangerous pathogens or biomolecules, including sites of possible biological or chemical weapons use.

In some embodiments, test samples can be directly applied to an electrophoretic medium. In other embodiments, however, the raw samples are subjected to standard sample preparation techniques, optionally including partial purification, which render the target molecules more accessible to binding partners during electrophoresis. For example, and without limitation, blood samples can be centrifuged to separate fractions including whole cells or membranes from serum, feces samples can be sectioned and homogenized with physiologically acceptable buffer and detergent (see, e.g., U.S. Pat. No. 5,741,650, U.S. Pat. No. 6,503,718), and sputum samples can be liquefied and fractionated. Antibiotics or bactericides optionally can be added to samples to prevent further growth of any organisms present. Whole cells can be removed or can be lysed to release their contents. For assays in which nucleic acids are to be detected, proteinases and inhibitors of DNA and RNA degrading enzymes optionally can be added. In addition, target molecules which are nucleic acids optionally can be amplified prior to detection. Alternatively, for assays in which proteins are to be detected, inhibitors of proteinases optionally can be added. Nucleic acids in test samples can be sheared or cut into smaller fragments (e.g., by mechanical shearing or restriction enzyme digestion), or can be amplified prior to electrophoresis by methods known in the art including, but not limited to, the polymerase chain reaction (PCR) and ligase chain reaction (LCR). Heterogeneous samples can be purified to remove substantially all non-nucleic acid molecules or substantially all non-protein molecules prior to loading the test sample into the electrophoretic medium. For example, and without limitation, nucleic acid samples can be extracted with phenol and chloroform. Many other standard techniques of nucleic acid and protein sample preparation are known in the art and can be found in, for example, Sambrook et al., eds., *Molecular Cloning: A Laboratory Manual,* 3rd Ed., Cold Spring Harbor Laboratory Press, Cold Spring Harbor, N.Y. (2001), and Watson et al., eds., *Recombinant DNA*, 2nd Ed., W.H. Freeman and Company, New York (1992), the entire disclosures of which are incorporated herein by reference.

In certain embodiments, the target molecules are mutated human nucleotide sequences which represent somatic cell mutations associated with cancers. For example, and without limitation, nucleotide sequences characteristic of colon cancer can be identified in feces, sequences characteristic of renal or bladder cancer can be identified in urine, sequences characteristic of retinoblastomas can be identified in vitreous humor, sequences characteristic of gliomas or neuroblastomas can be identified in cerebrospinal fluid, and sequences characteristic of breast cancer can be identified in mammary or axillary biopsies.

In other embodiments, the target molecules are allelic variants of human nucleotide sequences which are associated with genetic predispositions to disease or which are useful for forensic identification of individuals. For example, and without limitation, nucleotide sequences characteristic of predispositions to certain cancers can be identified in feces, blood or biopsy samples, sequences characteristic of specific individuals can be identified from blood, saliva, and semen samples obtained in criminal investigations; and sequences characteristic of specific haplotypes can be identified from amniotic fluid, or fetal or neonatal samples for paternity testing.

In other embodiments, the target molecules are pathogen-derived nucleic acids or proteins present in a test sample from an infected human subject. For example, and without limitation, nucleic acids or proteins characteristic of HIV-infection can be identified in a blood or plasma sample; nucleic acids or proteins characteristic of *Pseudomonas aeruginosa* or *Mycobacterium tuberculosis* infection can be identified in a sputum sample; or nucleic acids or proteins characteristic of infection with a sexually-transmitted disease can be identified in a semen sample.

In other embodiments, the target molecules are pathogen-derived nucleic acids or proteins present in a test sample from an environmental, industrial or commercial sample. For example, and without limitation, nucleic acids or proteins characteristic of HIV-infection can be identified in a sample from a blood or organ bank; nucleic acids or proteins characteristic of *Salmonella enteriditis* or *Escherichia coli* serotype 01 57:H7 contamination can be detected in food processing facilities; or proteins characteristic of *Vibrio cholerae* or coliform bacteria can be identified in water supplies.

Binding Partners

In some embodiments, the binding partner is a polynucleotide, an antibody, an aptamer, a receptor or a ligand. In each instance, the probe can be a naturally occurring molecule which is modified only to facilitate immobilization within the electrophoretic medium or for ease of detection, or can be a genetically or chemically engineered molecule which is modified for purposes of increased, decreased or altered selective binding affinity; increased, decreased or altered chemical or thermal stability; or other altered characteristics useful for the intended purpose.

The polynucleotide probes can be DNA probes, RNA probes, or polynucleotide probes having modified nucleoside bases or modified internucleoside linkages, whether known in the art or yet to be developed. Examples of modified nucleoside bases include, without limitation, the modified bases described in WIPO Standard ST.25 (1998), Appendix 2, Table 2, the entire disclosure of which is incorporated by reference herein (see also 37 C.F.R. 1.821-1.825). Examples of modified internucleoside linkages include, without limitation, modifications of the ribosyl or deoxyribosyl units such as halogenation, alkylation, alkoxylation or the like (e.g., 2-fluorination, 2-O-methylation, 5-methylation), modification or replacement of the phosphodiester linkages (e.g., substitution with phosphorothioate linkages), or modification or replacement of both the (deoxy)ribosyl and phosphate backbone (e.g., substitution with peptide nucleic acid (PNA) linkages). See, for example, Wetmur (1991), *Crit. Rev. Biochem. Mol. Biol.* 26:227-259; Moody et al. (1989), *Nucleic Acids Res.* 17:4769-4782; Iyer et al. (1995), *J. Biol. Chem.* 270: 14712-14717; Nielsen et al. (1991), *Science* 254:1497-1500.

In some embodiments, a polynucleotide probe has a length of between 15 and 200 bases. In certain embodiments, the polynucleotide probe has a length between 15 and 50 bases, between 50 and 80 bases, between 80 and 110 bases, between 110 and 140 bases, between 140 and 170 bases, or between 170 and 200 bases. Substantially longer binding partners also can be used.

Polynucleotide binding partners can be directed to sequences known to include nucleotide substitutions (including single nucleotide polymorphisms), deletions or insertions, or regions of microsatellite instability. For example, polynucleotide binding partners useful in the invention include, without limitation, those developed for the detection of BAT-26 sequences (see, e.g., U.S. Pat. No. 6,503,718), p 53 gene sequences (see, e.g., U.S. Pat. No. 5,527,676), MCC gene sequences (see, e.g., U.S. Pat. No. 5,330,892), APC gene sequences (see, e.g., U.S. Pat. No. 5,352,775; U.S. Pat. No. 6,503,718), DCC gene sequences (see, e.g., U.S. Pat. No. 5,532,108) and MET oncogene sequences (see, e.g., Li et a!. (2003), *Gene Ther. Mol. Biol,* 7:99-102).

Antibody binding partners can include naturally occurring antibodies produced or isolated from animals or cell culture, including polyclonal or monoclonal antibodies, Alternatively, antibody binding partners can include genetically engineered molecules, including chimeric antibodies, produced in recombinant organisms or cells, or can be chemically engineered molecules produced by chemical syntheses or degradation (e.g., cleavage or digestion). Antibody binding partners useful in the invention also include antibody fragments, such as Fab fragments, F(ab')$_2$ fragments, Fv fragments, or single-chain Fv fragments (scFv). Such antibody binding partners can be directed to epitopes known to include specific amino acid substitutions, deletions or insertions, or altered post-translational processing of proteins.

Antibodies may be produced by standard methods, well known in the art. See, e.g., Pluckthun, *Nature* 347:497-498 (1990); Huse et al, *Science* 246:1275-1289 (1989); Chaudhary et al., *Proc. Natl. Acad. Sci. USA* 87:1066-1070 (1990); Mullinax et al., *Proc. Natl. Acad. Sci. USA* 87:8095-8099 (1990); Berg et al., *Proc. Natl. Acad Sci. USA* 88:4723-4727 (1991); Wood et al., *J. Immunol.* 145:3011-3016 (1990); and references cited therein. Antibody binding partners useful in the invention include, without limitation, those specific for the detection of human carcinoma-associated antigens (see, e.g., PCT Intl. Pub. No. WO 96/08514), and prostate specific antigen (PSA).

Aptamer binding partners can be developed and selected by methods well known in the art (see, e.g., Tuerk et al. (1990), *Science.* 249:5050; Joyce (1989), *Gene* 82:83-87; Ellington et al. (1990), *Nature* 346:818-822; Klug et al. (1994), *Mol. Biol. Reports* 20:97-107), and can be used as binding partners against many kinds of analytes, including proteins, carbohydrates and small organic molecules.

Binding partners can be covalently bound to a region of the electrophoretic medium, can be bound to the medium ionically or by affinity binding, or can be trapped within the interstices of a medium comprising a cross-linked polymeric matrix.

A great variety of methods are known in the art for covalently binding partners such as polynucleotides or antibodies to various electrophoretic media. The methods can employ standard chemistries using reactive groups present on the binding partners and/or electrophoretic medium, or one or both of the binding partner and electrophoretic medium can be functionalized to add a desired reactive group. For example, and without limitation, carboxyl groups can be reacted with amine groups using carbodiimide conjugation reactions; primary amines can be reacted with other amine groups using glutaraldehyde; CNBr treatment can convert hydroxyl groups to cyanate ester or imidocarbonate groups which can be reacted with primary amines; and cyanuric chloride treatment can convert primary amines to chlorotriazines which can be reacted with primary ainines or thiols. For a review of useful conjugation reactions, see, e.g., Wong, ed., *Chemistry of Protein Conjugation and Cross-Linking*, CRC Press, Boca Raton, Fla. (1993).

Alternatively, binding partners can be conjugated to one member of an affinity binding pair such that the probes can be immobilized within an electrophoretic medium through a binding partner which is bound to the medium. Affinity binding pairs useful in this context include, without limitation, the biotin and streptavidin binding pair and the digoxigenin and antidigoxigenin binding pair. Thus, for example, and without limitation, binding partners can be conjugated to biotin to cause immobilization of the binding partners on beads coated with avidin or streptavidin. A packed volume of such beads can constitute an electrophoretic medium, or the beads can be intermixed with a polymeric matrix or gel to form a hybrid gel-bead electrophoretic medium. See, for example, U.S. Pat. No. 5,482,863, which describes methods for casting electrophoretic gels containing suspensions or particles. For antibody binding partners, the antibody itself can serve as an affinity binding partner with Protein A, which can be immobilized within the electrophoretic medium (see, e.g., Surolia et a!. (1981), *Trends Biochem. Sci.* 7:74). Alternatively, antibodies can be immobilized on Protein A-coated beads.

In other embodiments, binding partners can be functionalized with a monomer unit which is to be polymerized or co-polymerized to form an electrophoretic medium. When such modified binding partners are copolymerized with suitable mixtures of the monomers, polymeric media containing high concentrations of the immobilized binding partners can be produced. For example, and without limitation, binding partners functionalized with acrylamide groups (e.g., 5' acrylamide groups for polynucleotide binding partners) can be co-polymerized within a region of a polyacrylamide electrophoretic medium. Additional examples of methods for covalently attaching nucleic acids to polymerizable chemical groups are found in U.S. Pat. No. 5,932,711; U.S. Pat. No. 6,180,770; U.S. patent application Pub. No. 2002/0172955; U.S. patent application Pub. No. 2002/0197614 and PCI Intl. Pub. No. WO 98/51823. See also, Rehman et al. (1999), *Nucleic Acids Res.* 27:649; Bille et al. (1989), *Eur. J. Biochem.* 180:41-47; Wang et al. (1997), *Nature Biotechnology* 15:789-793; Holtz et al. (1997), *Nature* 389:829-832; Timofeev et al. (1996), *Nucleic Acids Res.* 24:3142-3148; and U.S. Pat. No. 5,478,893 for descriptions of other methods that have been used to immobilize proteins and small organic molecules within polymeric matrices and gels.

Electrophoretic Apparatus

An apparatus for electrophoresis typically includes an electrophoretic medium disposed within a non-conductive housing and at least one pair of electrodes for applying an electric field across the medium in a spatial dimension defined by the electrodes. The housing typically contains and defines the shape of an electrophoretic medium in the form of a substantially planar gel or, in capillary electrophoresis, a cylinder or capillary tube. Other shapes and conformations, however, can be used in accordance with the invention. In two-dimensional electrophoresis, a second pair of electrodes defines a second spatial dimension across the medium. See, generally, Giddings, ed., *Unified Separation Science*, John Wiley & Sons, New York (1991), p. 155-170.

With a conventional two-electrode apparatus for one-dimensional electrophoresis, reversal of the electric field can be achieved simply by switching the polarity of the two electrodes, as practiced in field inversion gel electrophoresis (Carle et al (1986), *Science* 232:65-68). Two-dimensional electrode arrangements, as used in pulsed field electrophoresis (see, e.g., Schwartz et al. (1984), *Cell* 3 7:67), allow the separation process of the present invention to be performed in two spatial dimensions, In principle, the addition of another set of electrodes operating in a third spatial dimension could add additional separation capability if desired.

The state of instrumentation and methodology for performing one- and two-dimensional electrophoretic separations is well advanced. At least one commercially available device (CHEF gel apparatus, Bio-Rad Life Science Research Products Catalog (1997), pp. 175-182) offers the capability of performing two-dimensional electrophoretic separations with programmable automated control of field orientation and pulse duration.

The present invention further provides an electrophoretic apparatus in which the electrophoretic medium includes at least two regions having distinct binding partners immobilized within each region. In some embodiments, the invention provides an electrophoretic apparatus or system in which the electrophoretic medium includes at least three regions having distinct binding partners immobilized within each region. In some embodiments comprising at least three regions, the binding partners in adjacent regions are distinct, but binding partners in non-adjacent regions can be the same.

The adjacent regions of the apparatus can be contiguous or can be separated by a void, spacer or separator that allows fluid communication between the regions. The apparatus can also include a sample inlet chamber to allow for introduction of a test sample, or a collection chamber to allow for removal of solvent and molecules which have eluted from the medium.

The apparatus can also include means for regulating the temperature of the entire electrophoretic medium or discrete regions.

The apparatus can also include a detector for detecting a sample front (i.e., the line of furthest advance of the sample through the medium) as it approaches a distal edge of the electrophoretic medium. Referring to FIG. 6, for example, if a sample is applied or introduced to the first region 201, electrophoresis will cause charged molecules to migrate through the second region 202 and into the third region 203. The detector can detect the sample as it reaches the distal edge of the third region 203, and cause the electric field to be reversed, thereby reversing the direction of electrophoresis. Another detector can be disposed at the opposite distal edge of first region 201 to detect the sample front as it returns and cause the electric field to reverse again, initiating another cycle of reversed field electrophoresis. A dye can be included in the test sample to facilitate detection by an optical detector. Alternatively, the detector can detect changes in resistance or conductivity caused by solutes in the sample.

The apparatus can also include a timer for reversing the electric field periodically. For example, once the period of time necessary for the sample front to reach the distal edge of the electrophoretic medium is determined, a timer can be set to periodically reverse the electric field after the determined period, or after a somewhat shorter or longer period.

The apparatus can also include a counter for tracking the number of cycles of reversed-field electrophoresis. For example, the counter can record or register each reversal of the electric field, and the counter can be set to signal (e.g., audibly, visibly or electronically) when a predetermined number of cycles has been reached, or to terminate the repetitive reverse-field electrophoresis when a predetermined number of cycles has been reached.

Systems for Repetitive Reversed-Field Affinity Electrophoresis

The present invention also provides systems for repetitive reversed-field affinity electrophoresis. Such systems include an electrophoretic apparatus, such as those described above, as well as other elements that can be used in the methods. For example, the systems can include a non-conductive housing for containing the electrophoretic medium, one or more pairs of electrodes disposed within the housing for applying an electric field across the medium in one or more spatial dimensions, and the electrophoretic medium itself.

In some embodiments, the electrophoretic medium includes at least two regions arranged in one spatial dimension, whereas in other embodiments the medium includes three or more regions arranged in one or more spatial dimensions. In each embodiment, at least one of the regions includes binding partners having selective binding affinity for target molecules and, in certain embodiments, at least one of the regions includes binding partners having selective binding affinity for non-target molecules.

In some systems, the electrophoretic medium includes at least three regions arranged in one spatial dimension, and each of the regions includes binding partners immobilized in that region and differing from the binding partners in each immediately adjacent region. In certain embodiments, at least two non-adjacent regions have identical binding partners. Thus, for example, and without limitation, the first and third regions can include differing or identical binding partners for non-target molecules and the second region can include binding partners for target molecules.

Optionally, the systems can include a detector for 'detecting a sample front as it approaches an edge of the electrophoretic medium. In certain embodiments, the systems include means for reversing the electric field after the detector detects the sample front.

Optionally, the systems can include a counter for tracking the number of cycles of reversed-field electrophoresis. In certain embodiments, the systems include means for signaling when a predetermined number of cycles has been reached or for terminating the repetitive reverse-field affinity electrophoresis when a predetermined number of cycles has been reached.

In certain embodiments, the systems also include at least one separator, such as a mesh or semi-permeable membrane, that separates different regions of the electrophoretic medium. Such separators are particularly useful for separating regions including packed volumes of beads to prevent migration of the beads during electrophoresis. Thus, in certain embodiments, the system includes a separator adjacent to at least one region of the electrophoretic medium that includes a packed volume of beads.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are embraced therein.

INCORPORATION BY REFERENCE

All publications and patent documents cited in this application are incorporated by reference in their entirety for all purposes to the same extent as if the contents of each individual publication or patent document was incorporated herein.

What is claimed is:

1. A system for repetitive reversed-field electrophoresis comprising:
    (a) a non-conductive housing for containing an electrophoretic medium;
    (b) at least one pair of electrodes disposed within said housing for applying an electric field across the medium in a spatial dimension defined by the electrodes;
    (c) an electrophoretic medium comprising at least two regions, wherein at least one of the regions comprises binding partners having selective binding affinity for target molecules; and
    (d) an apparatus configured for repetitively reversing the electric field to increase selective binding of the target molecules to their binding partners, wherein the apparatus configured for repetitively reversing the electric field comprises a detector for detecting a sample front as it approaches an edge of the electrophoretic medium.

2. A system for repetitive reversed-field electrophoresis as in claim 1, wherein at least one of the regions comprises binding partners having selective binding affinity for non-target molecules.

3. A system as in claim 1, wherein the electrophoretic medium comprises at least three regions; and wherein each of the regions includes binding partners immobilized in that region and differing from the binding partners in each immediately adjacent region.

4. A system as in claim 3, wherein at least two non-adjacent regions have identical binding partners.

5. A system for repetitive reversed-field electrophoresis as in claim 1, wherein the electric field is reversed after the detector detects the sample front.

6. A system as in claim 1, further comprising:
    (e) a counter for tracking a number of cycles of reversed-field electrophoresis.

7. A system for repetitive reversed-field electrophoresis as in claim 6, further comprising:
    (f) an apparatus configured for signaling when a predetermined number of cycles has been reached or for terminating the repetitive reverse-field electrophoresis when a predetermined number of cycles has been reached.

8. A system as in claim 1, further comprising:
    (e) at least one separator between adjacent regions of the electrophoretic medium.

9. A system as in claim 8 wherein at least one of the regions of the electrophoretic medium comprises a packed volume of beads.

10. A system as in claim 1, wherein the apparatus configured for repetitively reversing the electric field comprises a timer.

11. A system for repetitive reversed-field electrophoresis as in claim 10, wherein the timer is set to periodically reverse the electric field after a predetermined period.

12. A system as in claim 1, wherein the target molecules remain bound to their binding partners.

13. A system as in claim 1, wherein a constant voltage of electrophoresis is applied.

* * * * *